United States Patent [19]

Monte

[11] Patent Number: 4,734,123
[45] Date of Patent: Mar. 29, 1988

[54] NOVEL SULFONAMIDES AND METHOD OF MAKING

[75] Inventor: William T. Monte, Concord, Calif.

[73] Assignee: The Dow Chemical Company, Midland, Mich.

[21] Appl. No.: 860,159

[22] Filed: May 6, 1986

[51] Int. Cl.$^4$ ................. A01N 43/653; C07D 401/12; C07D 249/12; C07D 249/14
[52] U.S. Cl. .......................................... 71/92; 71/94; 71/103; 546/276; 548/263; 548/265; 548/266; 548/268
[58] Field of Search ............... 548/263, 265, 266, 264, 548/255; 71/92, 103, 94; 546/276

[56] References Cited

U.S. PATENT DOCUMENTS 2,670,282  2/1954  Allen ........................................ 71/92
2,914,536  11/1959  Hardy et al. ............................. 71/92
4,251,262  2/1981  Brookes et al. ...................... 548/265

Primary Examiner—Glennon H. Hollrah
Assistant Examiner—Patricia L. Morris
Attorney, Agent, or Firm—Merlin B. Davey

[57] ABSTRACT

N-aryl-5,6,7-substituted-1,2,4,-triazolo-[1,5-a]pyrimidine-2-sulfonamides undergo oxidative ring cleavage to afford herbicidal substituted N-aryl-5-amino-1,2,4-triazole-3-sulfonamides. These triazolesulfonamides can undergo cyclizations with 1,3-dicarbonyls to form novel herbicidal substituted N-aryl-5,6,7-substituted-1,2,4-triazolo-[1,5-a]pyrimidine-2-sulfonamides.

11 Claims, No Drawings

NOVEL SULFONAMIDES AND METHOD OF MAKING

BACKGROUND OF THE INVENTION

Compounds of the general structure I

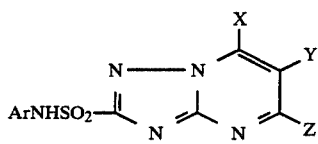

wherein Ar represents an aromatic (substituted or unsubstituted) or heteroaromatic (substituted or unsubstituted) ring system wherein the substituents are electron withdrawing functional groups in combination with other organic functional groups are exceptionally active herbicides and are active in the suppression of nitrification of ammonium nitrogen in soil and are effective in beneficially regulating the growth of crops and are readily produced. The aromatic ring may be monocyclic containing six carbon atoms or bicyclic containing ten carbon atoms. The heteroaromatic ring may be monocyclic containing five or six atoms or bicyclic containing nine or ten atoms. The heteroatoms present in the heteroaromatic ring may be one combination of one or more atoms such as nitrogen, oxygen, or sulfur.

Compounds in this family have been prepared by a conventional reaction between an appropriate substituted aniline and a substituted 1,2,4-triazolo-[1,5-a]-pyrimidine-2-sulfonyl chloride under basic conditions, as described in European patent application 142,152. However, it is difficult to prepare many analogs in high yield due to the poor compatability of the heterocycle substituents (X, Y, and Z) to the reaction conditions for the preparation of the sulfonyl chloride or the subsequent sulfonamide (I).

SUMMARY OF THE INVENTION

This invention provides a new method for the preparation of compounds of type I which eliminates most of the shortcomings of the methodology which had been previously described. The new method of this invention proceeds through novel herbicidal intermediates as described more fully hereinafter.

DETAILED DESCRIPTION OF THE INVENTION

The novel procedure for the preparation of compounds of formula I is illustrated in Scheme I. The starting N-aryl-1,2,4-triazolo-[1,5-a]pyrimidine-2-sulfonamides (II), where A, B, and C independently represent H, $C_1$–$C_4$ alkyl, $C_1$–$C_4$ haloalkyl, $C_1$–$C_4$ alkoxy, $C_1$–$C_4$ haloalkoxy, halo (F, Cl, Br, I) or amino (including alkyl or aryl substituted amino) are available via the conventional methodology described in European patent application No. 142,152, which is incorporated herein by reference.

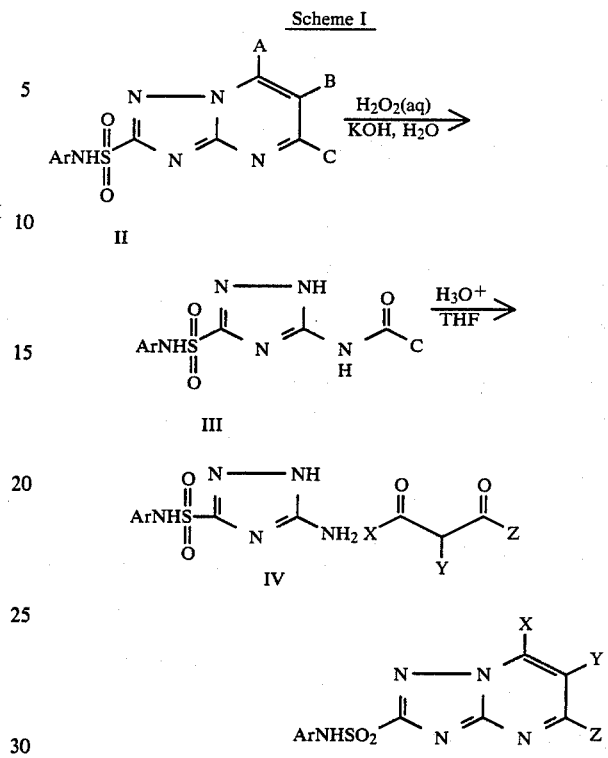

In accordance with this invention the sulfonamides (II) can be oxidized with a variety of transition metal oxidants, peracids or peroxides (i.e., $KMnO_4$, $CrO_3$, peracetic acid, or hydrogen peroxide). the sulfonamides II can best be oxidized with 2 to 15 equivalents of 30–37 percent hydrogen peroxide in the presence of 2 to 5 equivalents of 0.1 to 1.0 molar aqueous alkali metal hydroxide (i.e. KOH or NaOH) solution as a solvent. The reaction may be run at temperatures ranging from ambient temperature to reflux. In the case where hydrogen peroxide was used as the oxidant the reaction was commonly run at 22° C. to 35° C. The products of this transformation (III) were usually isolated as their neutral species by acidification of the reaction mixture. The reaction mixture is then treated with $SO_2$ (or $NaHSO_3$) until a negative peroxide test is observed and the product is collected by filtration. This method offers a facile workup procedure requiring no additional handling of spent oxidant salts and consistantly gives superior yields of a product possessing suitable purity as to be used in subsequent reactions without further purification. In addition, the hydrogen peroxide oxidative method is mild enough to be compatible with most functionalities ($R^1$, $R^2$, $R^3$, $R^4$, and $R^5$) desired on the phenyl nucleus (e.g. methyl). In cases where $R^1$, $R^2$, $R^4$, and $R^5$ are functionalities which are incompatible with the oxidation conditions (e.g., $-SR^7$, $-SOR^7$) or the subsequent hydrolysis reaction (e.g., $-COOR^9$, $-CN$) of the above described invention, they can be achieved by transforming appropriate compatible $R^1$, $R^2$, $R^4$, $R^5$ to the desired functionalities by commonly known methods known to those versed in the art.

The sulfonamides (II) could also be oxidized with 2 to 5 equivalents of potassium permanganate in the presence of 2 to 5 equivalents of 0.1 to 1.0 molar aqueous alkali metal hydroxide (i.e. KOH or NaOH) solution as a solvent. The reaction may be run at temperatures ranging from ambient temperature to reflux. The reaction is most commonly run at 50° C. to 60° C. for the case when potassium permanganate is used as the oxidant. The products of this transformation (III) are usually isolated as their neutral species by removing the spent manganese oxidant by filtration followed by acidification of the filtrate; or by acidification of the reaction mixture, and then addition of $SO_2$ (or $NaHSO_3$) to solubilize the spent manganese oxidant and collection of the product by filtration. This oxidation procedure has the limitation that certain functionalities (e.g. ortho methyl) on the phenyl portion of the sulfonamides (II) are reactive under the reaction conditions.

The N-acylated product (III) from the oxidative degradation can be hydrolyzed by aqueous acid hydrolysis in the presence of an organic co-solvent. The aqueous acid solutions can be used in 1 to 6 molar concentrations. Common readily available acids which are effective in this transformation include both mineral (i.e. HCl or $H_2SO_4$) or organic (i.e. acetic acid, trifluoroacetic acid, or methanesulfonic acid) acids. The volume ratio of aqueous acid to organic co-solvent can vary from 1 to 0.1. A ratio which solubilizes the starting material is usually chosen. Appropriate organic co-solvents include acetone, methyl ethyl ketone, ethanol, acetonitrile, or tetrahydrofuran (THF). The free amino product (IV) is isolated as its neutral species or acid salt after solvent removal. This crude product (IV) may be purified by recrystallization or used directly in subsequent transformations without purification.

Herbicidal compounds prepared by the process of this invention have the general formula:

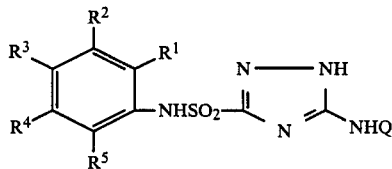

wherein $R^1$ represents halo (F, Cl, Br, I), $-NO_2$, -phenyl, OAr, $-CF_3$, $-OCF_3$, $-OCF_2CF_2H$, $-OCF_2CCl_2H$, $-OCH_2CF_3$, $-SO_2CF_3$, $-SO_2CF_2CF_2H$, $-SO_2CF_2CCl_2H$, $-SO_2R^6$, $-COOH$, $-CONH_2$, $-CONHR^7$, $-CONR^7(R^8)$, $-SO_3R^7$, and $-SO_3CH_2CF_3$; $R^2$ and $R^4$ represent H, halo (F, Cl, Br, I), $C_1-C_4$ alkyl, $-COOH$ and $-OR^7$; $R^3$ is H; and $R^5$ represents H, $C_1$ to $C_4$ alkyl, halo (F, Cl, Br, I), $-NO_2$, $-CF_3$, $-OCF_3$, $-OCF_2CF_2H$, $-OCF_2CCl_2H$, $-OCH_2CF_3$, $-SO_2CF_3$, $-SO_2CF_2CF_2H$, $-SO_2CF_2CCl_2H$, $-COOH$, $-CONH_2$, $-CONHR^7$, $CONR^7(R^8)$, $-SO_2R^7$, $-SO_2CH_2CF_3$, $-NR^6R^6$, and $-CR^6R^6OR^6$, wherein Ar represents substituted or unsubstituted aryl or substituted or unsubstituted heteroaryl, $R^6$ represents H, aryl or $C_1-C_4$ alkyl, and $R^7$ and $R^8$ individually represent $C_1-C_4$ alkyl; and Q represents H or COX where X represents H, $C_1-C_6$ alkyl, or substituted alkyl.

Scheme II

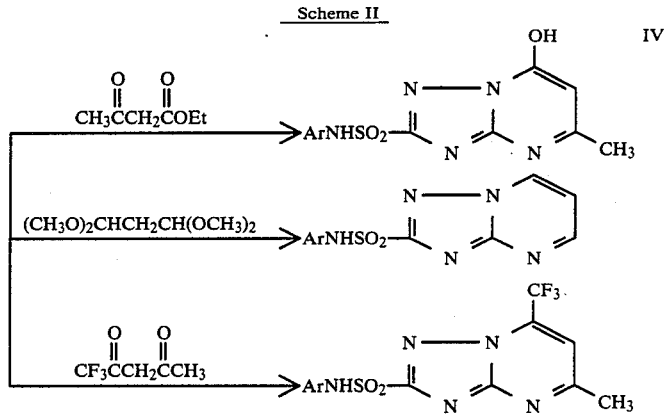

The final step in this sequence for the conversion of compound IV to I, detailed in Scheme II, may be carried out by reacting compound IV with various 1,3-dicarbonyls or 1,3-dicarbonyl equivalents using methodology generally outlined in "Heterocyclic Systems with Bridgehead Nitrogen Atoms", Part Two, W. L. Mosby, Interscience Publisher, 1961, p. 878. A wide variety of 1,3-dicarbonyl compounds may be used in this reaction which may be run under acidic (i.e. acetic acid as a solvent), neutral (i.e. n-butanol, dimethylformamide, dimethylsulfoxide, or tetrahydrofuran as a solvent) or basic conditions (i.e. using alkali metal alkoxides or carbonates in polar (i.e. ethanol or dimethylformamide (DMF)) solvents. Suitable 1,3-dicarbonyls include 1,3-diketones, β-keto esters, malonic esters, malonaldehyde, β-ketoaldehydes, or α-formyl esters or derivatives thereof (i.e., acetals or enol

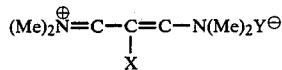

ethers). Additionally, condensations involving methaniminium compounds of type V are useful in the synthesis of a number of 6-substituted 1,2,4-triazolo-[1,5-a]-pyrimidine-2-sulfonamides.

In instances where the 1,3-dicarbonyl compound is unsymmetrical, the possibility of obtaining two different isomers from condensation with IV exists. As described in European Patent Application No. 142,152, the exocyclic nitrogen in IV is generally the first to condense with the 1,3-dicarbonyl compound under neutral or acidic conditions. Under basic conditions the endocyclic nitrogen in IV is sometimes more reactive. Consequently, in situations where a clear difference in reactivity of the two carbonyl functionalities in the 1,3-dicarbonyl compound exists, some measures of regiochemical control may be achieved by choice of reaction conditions.

In the synthetic routes listed above, compounds of type I where X and/or Z is OH are capable of undergoing further transformation (e.g. Scheme III). For example, treatment of compound I (X and/or Z=OH) with phosphorus oxychloride yields I (X and/or Z=Cl). The reaction is generally carried out at reflux in neat phosphorus oxychloride or with phosphorous oxychloride in a solvent (i.e. acetonitrile). Compound I (X and/or Z=Cl) can be further reacted with nucleophiles (i.e. NaOCH$_3$, MeMgBr, NaSMe) to yield I (X and/or Z=OCH$_3$, CH$_3$, or SMe respectively). In addition compound I (X and/or Z=Cl) may be reduced to afford I (X and/or Z=H). An effective reducing agent for this type of transformation is zinc-copper couple in the presence of acid.

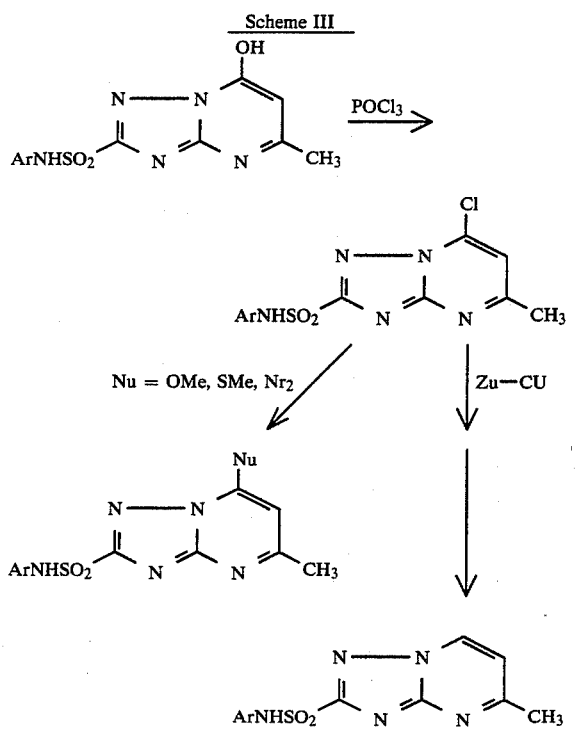

Herbicidal compounds prepared by this embodiment of this invention have the general formula:

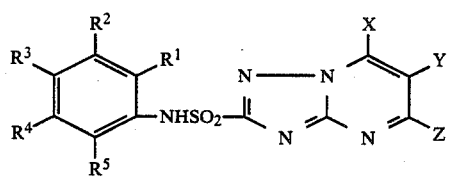

wherein R$^1$ thru R$^5$ represents H, halo (F, Cl, Br, I), —NO$_2$, phenyl, —OAr, —CF$_3$, —OCF$_3$, —OCF$_2$CF$_2$H, —OCF$_2$CCl$_2$H, —OCH$_2$CF$_3$, —SO$_2$CF$_3$, —SO$_2$CF$_2$CF$_2$H, —SO$_2$CF$_2$CCl$_2$H, —SO$_2$R$^6$, —COOR$^6$, —CONH$_2$, —CONHR$^7$, —CONR$^7$(R$^8$), —SO$_3$R$^7$, and —SO$_3$CH$_2$CF$_3$, C$_1$-C$_4$ alkyl, and —OR$^7$, and —SR$^6$, —CR$^6$R$^6$OR$^6$, —NR$^6$R$^6$, wherein Ar represents substituted or unsubstituted aryl or substituted or unsubstituted heteroaryl, R$^6$ represents H, aryl or C$_1$-C$_4$ alkyl, and R$^7$ and R$^8$ individually represent C$_1$-C$_4$ alkyl; and X, Y, and Z represent H, C$_1$-C$_6$ alkyl, alkenyl, aryl, substituted alkyl or substituted aryl, C$_1$-C$_6$ alkoxy or substituted alkoxy, phenoxy or substituted phenoxy, CONHR$^7$, CONR$^7$(R$^8$), —COOR$^6$, —CN; or X and Y or Y and Z can be joined to form a cycloalkyl ring (i.e., —(CH$_2$)n— wherein n is 3 or 4) wherein the ring can contain a heteroatom (i.e., O, N, or S) and or unsaturation (—CO— or —C=C—).

Compounds advantageously prepared by the process of this invention are these wherein R$^1$ represents H, halo (F, Cl, Br, I), —NO$_2$, —phenyl, —OAr, —CF$_3$ —OCF$_3$, —OCF$_2$CF$_2$H, —OCF$_2$CCl$_2$H, —OCH$_2$CF$_3$, —SO$_2$CF$_3$, —SO$_2$CF$_2$CF$_2$H, —SO$_2$CF$_2$CCl$_2$H, —SO$_2$R$^6$, —COOH, —COOR$^6$, —CONH$_2$, —CONHR$^7$, —CONR$^7$(R$^8$), —SO$_3$R$^7$, and —SO$_3$CH$_2$CF$_3$; R$^2$ and R$^4$ represent H, halo (F, Cl, Br, I), C$_1$-C$_4$ alkyl, —COOH and —OR$^7$; R$^3$ is H; and R$^5$ represents H, halo (F, Cl, Br, I), —NO$_2$, —CF$_3$, —OCF$_3$, —OCF$_2$CF$_2$H, —OCF$_2$CCl$_2$H, —OCH$_2$CF$_3$, —SO$_2$CF$_3$, —SO$_2$CF$_2$CF$_2$H, —SO$_2$CF$_2$CCl$_2$H, —COOR$^6$, —CONH$_2$, —CONHR$^7$, —CONR$^7$(R$^8$), —SO$_2$R$^7$, —SO$_2$CH$_2$CF$_3$, —NR$^6$R$^6$, and —CR$^6$-R$^6$OR$^6$, wherein Ar represents substituted or unsubstituted aryl or substituted or unsubstituted heteroaryl, R$^6$ represents H, aryl or C$_1$-C$_4$ alkyl, and R$^7$ and R$^8$ individually represent C$_1$-C$_4$ alkyl; and X, Y, and Z represent H, halogen (Cl), —SR$^6$, —OR$^7$, —NR$^6$R$^6$, hydroxy, —COOR$^6$, —CONH$_2$, —CONHR$^7$, —CONR$^7$(R$^8$), CF$_3$.

Compounds most advantageously prepared by these transformations are those wherein R$^1$ and R$^5$ represent H, C$_1$-C$_4$ alkyl, halo (F, Cl, Br, I), —NO$_2$, —phenyl, —OAr, —CF$_3$ —OCF$_3$, —OCF$_2$CF$_2$H, —OCF$_2$CCl$_2$H, —OCH$_2$CF$_3$, —SO$_2$CF$_3$, —SO$_2$CF$_2$CF$_2$H, —SO$_2$CF$_2$CCl$_2$H, —SO$_2$R$^6$, —CN, —COOR$^6$, —CONH$_2$, —CONHR$^7$, —CONR$^7$(R$^8$), —SO$_3$R$^7$, —SO$_3$CH$_2$CF$_3$ and —CR$^6$R$^6$ OR$^6$; R$^2$ and R$^4$ represent H, halo (F, Cl, Br, I), C$_1$-C$_4$ alkyl, —COOR$^6$, and —OR$^7$; and R$^3$ is H; wherein Ar represent substituted or unsubstituted aryl or substituted or unsubstituted heteroaryl, R$^6$ represents H, aryl or C$_1$-C$_4$ alkyl, and R$^7$ and R$^8$ individually represent C$_1$-C$_4$ alkyl; and X, Y, and Z represent H, C$_1$-C$_4$ alkyl, C$_1$-C$_4$ alkoxy, —CF$_3$, and —SR$^7$.

The following examples serve to illustrate the invention:

EXAMPLE 1
N-(2,6-dichlorophenyl)-5-acetamido-1,2,4-triazole-3-sulfonamide

Method A

A solution of 52.0 g (140 mol) of N-(2,6-di-chlorophenyl)-5,7-dimethyl-1,2,4-triazolo-[1,5-a]pyrimidine-2-sulfonamide in 2000 ml of 0.44 M aqueous potassium hydroxide was treated with 110.3 g (689 mol) of potassium permaganate. The suspension was stirred for one hour at 60° C. The brown suspension was then cooled and poured into 1000 g of ice. The mixture was carefully acidified with concentrated hydrochloric acid to a pH of approximately three. To this acid solution was added sodium bisulfite in small portions until all the brown magnesium dioxide was dissolved leaving a white solid in an acidic yellow solution. The solid was collected, redissolved in 0.5 N NaOH and then acidified with 3 N aqueous HCl. The solid was collected and dried to yield 30.0 g (61 percent) of the desired product as a white solid, mp 312°–314° C. (decomposition). IR, $^1$H NMR, and $^{13}$C NMR were consistent with the assigned structure.

Method B

To a solution of 86.0 g (0.23 mol) of N-(2,6-dichloro)-phenyl-5,7-dimethyl-1,2,4-triazolo-[1,5-a]pyrimidine-2-sulfonamide and 53.0 g (0.95 mol) of potassium hydroxide in 2.5 l of water was added 250 ml (2.6 mol) of 35 percent aqueous peroxide via dropwise addition maintaining the temperature at 30°–35° C. After 1 hour the dark brown solution lightened to a pale yellow color and by TLC (20 percent methanol-methylene chloride) all the starting material had been consumed. The solution was then carefully acidified with 6N aqueous HCl and excess peroxide decomposed by addition of sodium sulfite until a negative peroxide paper test was observed. The resulting solid was collected and dried. Recovered 68.0 g (84 percent) of a white solid which was identical to previously made material. This material was pure enough to be taken on directly to the hydrolysis step.

Analysis: Calculated for $C_{10}H_9Cl_2N_5O_3S$: C, 34.28; H, 2.57; N, 20.0. Found: C, 34.12; H, 2.55; N, 20.13

EXAMPLE 2

Preparation of N-(2,6-difluoro-3-methylphenyl)-5-formamido-1,2,4-triazole-3-sulfonamide A solution of 4.0 g (12.3 mmol) of N-(2,6-difluorophenyl)-1,2,4-triazolo-[1,5-a]pyrimidine-2-sulfonamide in 120 ml of water containing 2.8 g (50 mmol) of potassium hydroxide. To this solution was added 14 ml of 37 percent aqueous hydrogen peroxide via dropwise addition. A mild exotherm resulted and the rate of addition of the oxidant was used to keep the temperature between 30°–35° C. After 1 h the light yellow solution was acidified with 6N aqueous HCl and excess oxidant decomposed by addition of sodium sulfite until a negative peroxide paper test was achieved. The resulting solid was collected to afford 3.2 g (82 percent) as a white powder; mp 270°–273° C. Analysis: Calculated for $C_{10}H_9F_2N_5O_3S$: C, 37.85; H, 2.86; N, 22.08. Found: C, 37.39; H, 2.85; N, 22.00.

EXAMPLE 3

Preparation of N-(2-chloro-6-methylphenyl)-5-formamido-1,2,4-triazole-3-sulfonamide A solution of 4.0 g (11.8 mmol) of N-(2-chloro-6-methylphenyl)-6-methyl-1,2,4-triazolo-[1,5-a]pyrimidine-2-sulfonamide in 120 ml of water containing 2.7 g (49 mmol) of potassium hydroxide. To this solution was added 14 ml of 35 percent aqueous hydrogen peroxide via dropwise addition. A mild exotherm resulted and the rate of addition of the oxidant was used to keep the temperature between 30°–35°. After 1 h the light yellow solution was acidified with 6N aqueous HCl and excess oxidant decomposed by addition of sodium sulfite until a negative peroxide paper test was achieved. The resulting solid was collected and again dissolved in 50 ml of ethanol and a minimum amount of aqueous saturated bicarbonate. The solution was acidified with aqueous HCl to afford 3.0 g (80 percent) of product as a white powder; mp 291°–300° C. decomposition.

Analysis: Calculated for $C_{10}H_{10}ClN_5O_3S$: C, 38.04; H, 3.19; N, 22.8. Found: C, 37.79; H, 3.2; N, 22.17.

EXAMPLE 4

N-(2,6-dichlorophenyl)-5-amino-1,2,4-triazole-3-sulfonamide

A solution of 45.0 g (0.13 mol) of N-(2,6-dichlorophenyl)-5-acetamido-1,2,4-triazole-3-sulfonamide, 60 ml of 6N aqueous hydrochloric acid, and 500 ml of THF was heated at reflux for 4 hrs. The reaction mixture was cooled and the solvent was removed by rotary evaporation in vacuo. The crude solid was triturated with 5 ml of cold ethanol and then recrystallized from water. The desired product was collected by filtration and dried to yield 34.0 g (86 percent) of the desired product as a white solid, mp 262°–264° C. (decomposition). IR, $^1H$ NMR, and $^{13}C$ NMR were consistent with the assigned structure.

Analysis: Calculated for $C_8H_7Cl_2N_5O_2S$: C, 31.17; H, 2.27; N, 22.73. Found: C, 31.38; H, 2.30; N, 22.89.

EXAMPLE 5

N-(2,6-dichlorophenyl)-1,2,4-triazolo-[1,5-a]pyrimidine-2-sulfonamide

A suspension of 2.0 g (6.5 mmol) of N-(2,6-dichlorophenyl)-5-amino-1,2,4-triazolo-3-sulfonamide in 75 ml of n-butanol containing 2 ml of acetic acid was heated until the mixture was homogeneous. To this solution was added 1.43 g (1.56 ml, 6.5 mmol) of malonaldehyde bis(diethyl acetal) and the solution was heated at reflux for 20 hours. The mixture was cooled and the resulting solid was collected by filtration, washed with cold butanol, and dried to yield 1.5 g (67 percent) of the desired product as a white solid, mp 278°–280° C. IR, $^1H$ NMR, and $^{13}C$ NMR were consistent with the assigned structure.

Analysis: Calculated for $C_{11}H_7Cl_2N_5O_2S$: C, 38.38; H, 2.03; N, 20.35. Found: C, 38.28; H, 1.70; N, 20.75.

EXAMPLE 6

N-(2,6-dichlorophenyl)-5-methyl-7-trifluoromethyl-1,2,4-triazolo-[1,5-a]pyrimidine-2-sulfonamide A hot solution of 2.0 g (6.5 mmol) of N-(2,6-dichlorophenyl)-5-amino-1,2,4-triazolo-3-sulfonamide in 75 ml of glacial acetic acid was treated with 1.02 g (0.8 ml, 6.6 mmol) of 1,1,1-trifluoro-2,4-pentanedione and heated at 100° C. for 20 hours. On cooling a solid formed and was collected by filtration and dried to afford 2.5 g (90 percent) of the desired product as a white solid, mp 237°–239° C. IR, $^1H$ NMR, and $^{13}C$ NMR were consistent with the assigned structure.

Analysis: Calculated for $C_{13}H_8Cl_2F_3N_5O_2S$: C, 36.63; H, 1.88; N, 16.43. S, 7.53. Found: C, 36.74; H, 1.52; N, 16.94. S, 7.71

EXAMPLE 7

N-(2,6-dichlorophenyl)-7-hydroxy-5-methyl-1,2,4-triazolo-[1,5-a]pyrimidine-2-sulfonamide A solution of 5.0 g (14.3 mmol) of N-(2,6-dichlorophenyl)-5-amino-1,2,4-triazol-3-sulfonamide, 0.5 ml of acetic acid, and 2.0 ml (15.6 mmol) of ethyl acetoacetate in 100 ml of absolute methanol was heated at reflux for 48 hr. After 24 hr a solid began to form. The solution was cooled and the solid collected. After drying, 4.0 g (75 percent) of the desired product was obtained as a white powder; mp 302° C. decomposes.

Analysis: Calculated for $C_{12}H_9Cl_2N_5O_2S$: C, 38.51; H, 2.41; N, 18.72. Found: C, 38.52; H, 2.49; N, 19.03.

EXAMPLE 8

N-(2,6-dichlorophenyl)-7-chloro-5-methyl-1,2,4-triazolo-[1,5-a]pyrimidine-2-sulfonamide A suspension of 10.0 g (27.0 mmol) of N-(2,6-dichlorophenyl)-7-hydroxy-5-methyl-1,2,4-triazolo-[1,5-a]-pyrimidine-2-sulfonamide and 100 ml (1.1 mol) of phosphorous oxychloride in 700 ml of acetonitrile (dried over 4A Molecular Sieves) was heated at reflux for 24 hr. As the reaction progressed the mixture became homogeneous. After cooling the solution was concentrated by rotary evaporation in vacuo and the resulting residue was diluted with 300 ml of methylene chloride and 10 ml of water. The methylene chloride solution was decanted off and the solid that had formed was triturated with 100 ml of hexane and 5 ml of water. The resulting yellow solid was collected. Recovered 9.0 g (85 percent) of the desired product; mp 217°–220° C. An analytical sample could be prepared by recrystallization from methanol (mp 218°–221° C.).

Analysis: Calculated for $C_{12}H_8Cl_3N_5O_2S$: C, 36.70; H, 2.04; N, 17.84. Found: C, 36.69; H, 2.13; N, 17.93.

EXAMPLE 9

N-(2,6-dichlorophenyl)-7-methoxy-5-methyl-1,2,4-triazolo-[1,5-a]pyrimidine-2-sulfonamide A sodium methoxide-methanol solution was made by dissolving 0.3 g (13 mg-atom) of sodium metal into 20 ml of absolute methanol. To this solution was added 1.0 g (2.5 mmol) of N-(2,6-dichlorophenyl)-7-chloro-5-methyl-1,2,4-triazolo-[1,5-a]pyrimidine-2-sulfonamide. A mild exotherm ensued and the reaction was complete within 10 min as determined by TLC (20 percent methanol-methylene chloride). The solution was acidified with 6N aqueous HCl and the resulting white solid collected. Recovered 0.9 g (93 percent) of a white powder; mp 214°–215° C.

Analysis: Calculated for $C_{13}H_{11}Cl_2N_5O_3S$: C, 40.21; H, 2.84; N, 8.04. Found: C, 39.84; H, 3.08; N, 17.99.

EXAMPLE 10

N-(2,6-dichlorophenyl)-7-methylthio-5-methyl-1,2,4-triazolo-[1,5-a]pyrimidine-2-sulfonamide A sodium methylmercaptan-dimethylsulfoxide (DMSO) solution was prepared by adding 0.3 g (6.2 mmol) of methylmercaptan to a mixture of 0.3 g (6.2 mmol) of a 50 percent oil dispersion of sodium hydride in 20 ml of DMSO. To this solution was added 1.0 g (2.5 mmol) of N-(2,6-dichlorophenyl)-7-chloro-5-methyl-1,2,4-triazolo-[1,5-a]pyrimidine-2-sulfonamide and the mixture was stirred for 15 minutes at room temperature. A mild exotherm began on addition and the reaction was complete within 15 minutes. The reaction was then acidified with 6N aqueous HCl and then diluted with 50 ml of water. The resulting white solid was collected and dried to afford 1.0 g (98 percent) of desired product; mp 300°–305° C. decomposes. An analytical sample was prepared by base-acid reprecipatation.

Analysis: Calculated for $C_{13}H_{11}Cl_2N_5O_2S_2$: C, 38.61; H, 2.72; N, 17.32. Found: C, 38.99; H, 2.93; N, 17.34.

EXAMPLE 11

N-(2,6-dichlorophenyl)-5-chloro-1,2,4-triazolo-[1,5-a]pyrimidine-2-sulfonamide

A solution of 2.0 g (4.8 mmol) of N-(2,6-di-chlorophenyl)-5,7-dichloro-1,2,4-triazolo-[1,5-a]-pyrimidine-2-sulfonamide, 20 ml of tetrahydrofuran, 1 of glacial acetic acid, and 1 ml of methanol was treated with 1.0 g of zinc-copper couple (Bradly, W. T. JOC 1966, 31, 626 and Fieser & Fieser, "Organic Reagents"; John Wiley & Sons, N.Y., 1967; Vol. 1, p. 1287). A mild exotherm occurred and the reaction was vigorously stirred. The reaction was monitored by TLC (20 percent MeOH-CH$_2$Cl$_2$) and after 18 hr some starting material was still present. At this time 3 drops of concentrated HCl was added and stirring was continued for an additional 24 hr. The mixture was filtered and the zinc cake washed with methylene chloride. The filtrate was diluted with 50 ml of hexane which induced formation of a solid. The solid was collected to afford 0.7 g (38 percent) of the product as the zinc chloride salt as an orange solid. The neutral product was prepared by stirring the salt in a 3M aqueous HCl solution for 5 min and then collecting the yellow solid; mp 291°–300° C. decomposition.

Analysis Calculated for $C_{11}H_6Cl_3N_5O_2S \cdot ZnCl$: C, 27.53; H, 1.25; N, 14.60. Found: C, 27.49; H, 1.54; N, 14.62.

EXAMPLE 12

N-(2,6-dichlorophenyl)-5,7-dihydroxy-1,2,4-triazolo-[1,5-a]pyrimidine-2-sulfonamide A solution of 8.0 g (26 mmol) of N-(2,6-dichlorophenyl)-5-amino-1,2,4-triazolo-2-sulfonamide, 17.6 ml (80 mmol) of a 25 percent sodium methoxide-methanol solution, and 6 ml (52 mmol) of dimethyl malonate in 200 ml of absolute ethanol was heated at reflux. After 48 hours no starting material was detected by TLC (20 percent methanol-methylene chloride). The resulting sodium salt was collected by filtration and then dissolved in 100 ml of water. The solution was acidified with 6N aqueous HCl and the resulting solid was collected and dried to afford 4.6 g (47 percent) of a white powder; mp 306°–308° C., discolors at 262° C.

Analysis: Calculated for $C_{11}H_7Cl_2N_5O_4 \cdot H_2O$: C, 33.51; H, 2.3; N, 17.77. Found: C, 33.27; H, 2.5; N, 18.04.

EXAMPLE 13

N-(2,6-dichlorophenyl)-5,7-dichloro-1,2,4-triazolo-[1,5-a]pyrimidine-2-sulfonamide A suspension of 4.0 g (11.0 mmol) of N-(2,6-dichlorophenyl)-5,7-dihydroxy-1,2,4-triazolo-[1,5-a]-pyrimidine-2-sulfonamide and 5.0 ml (33 mmol) phosphorous oxychloride in 200 ml of acetonitrile (dried over 4A molecular sieves) was heated at reflux for 22 hours. As the reaction progressed the mixture became homogeneous. After cooling the solution was concentrated by rotary evaporation in vacuo and the resulting residue was diluted with 100 ml of methylene chloride and 10 ml of water. After stirring for 5 minutes a solid formed and the resulting yellow solid was collected to afford 2.0 g (44 percent) of the desired product; mp 154°–210° decomposition.

Analysis: Calculated for $C_{11}H_5Cl_4N_5O_2S$: C, 31.98; H, 1.72; N, 16.96. Found: C, 31.54; H, 1.77; N, 17.41.

EXAMPLE 14

N-(2,6-dichlorophenyl)-5,7-dimethoxy-1,2,4-triazolo-[1,5-a]pyrimidine-2-sulfonamide A solution of 20 ml (9.6 mmol) of sodium methoxide-methanol was treated with 1.0 g (2.4 mmol) of N-(2,6-dichlorophenyl)-5,7-dichloro-1,2,4-triazolo-[1,5-a]pyrimidine-2-sulfonamide and was stirred for 15 minutes at 25°–30° C. The solution was acidified with 6N aqueous HCl and then concentrated by rotary evaporation in vacuo. The residue was washed with water and then triturated with warm isopropanol (2X) to afford 0.4 g (41 percent) of a white powder; mp 232°–234° C. decomposition.

Analysis: Calculated for $C_{13}H_{11}Cl_2N_5O_4S$: C, 38.62; H, 2.74; N, 17.33; S, 7.93. Found: C, 37.91; H, 2.77; N, 17.72; S, 8.26.

Following the above general procedures and employing appropriate starting materials the compounds indicated in the table below were prepared.

TABLE I

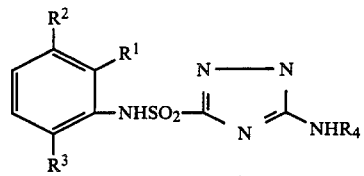

| No. | $R^1$ | $R^2$ | $R^3$ | $R^4$ | MP | Anal C | Found C | Anal H | Found H | Anal N | Found N |
|---|---|---|---|---|---|---|---|---|---|---|---|
| 1 | Cl | H | Cl | COME | 312–314DE | 34.28 | 34.12 | 2.57 | 2.55 | 20.0 | 20.13 |
| 2 | Cl | H | Cl | H | 263–264DE | 31.17 | 31.96 | 2.27 | 2.3 | 22.73 | 22.35 |
| 3 | $CF_3$ | H | OME | H | 185–206DE | 31.19 | 30.89 | 3.19 | 3.35 | 18.19 | 17.76 |
| 4 | F | ME | F | H | 166–168 | 33.18 | 33.4 | 3.09 | 3.24 | 21.50 | 21.55 |
| 5 | F | H | F | H | 224–225 | 30.82 | 30.60 | 2.59 | 2.65 | 22.47 | 22.7 |
| 6 | Cl | ME | Cl | H | 206–208 | 30.14 | 29.9 | 2.81 | 3.33 | 19.33 | 18.97 |
| 7 | Cl | H | ME | H | 239–241 | 37.57 | 37.56 | 3.50 | 3.40 | 24.34 | 24.72 |
| 8* | F | H | F | COME | 292–296 | 37.63 | 37.92 | 3.4 | 2.89 | 21.95 | 22.4 |
| 9 | F | ME | F | COH | 270–273 | 37.85 | 37.39 | 2.86 | 2.85 | 22.08 | 22.00 |
| 10 | Cl | ME | Cl | COME | 286–287 | 36.17 | 36.2 | 3.01 | 3.12 | 19.18 | 19.59 |
| 11* | F | ME | F | COME | 273–275 | 39.6 | 38.9 | 3.90 | 3.24 | 21.01 | 21.07 |
| 12* | $CF_3$ | H | OME | COME | 291–296 | 38.09 | 37.66 | 2.91 | 3.18 | 18.52 | 18.48 |
| 13 | Cl | H | ME | COH | 291–300DE | 38.04 | 37.74 | 3.19 | 3.2 | 22.18 | 22.17 |

TABLE II

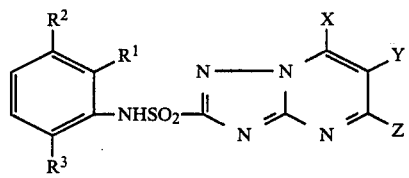

| No. | $R^1$ | $R^2$ | $R^3$ | X | Y | Z | MP | Cal C | Found C | Cal H | Found H | Cal N | Found N |
|---|---|---|---|---|---|---|---|---|---|---|---|---|---|
| 14 | Cl | H | Cl | $CF_3$ | H | ME | 237–239 | 36.63 | 36.74 | 1.88 | 1.52 | 16.42 | 16.94 |
| 15 | Cl | H | Cl | H | H | H | 278–280 | 38.38 | 38.28 | 2.03 | 1.70 | 20.35 | 20.75 |
| 16 | Cl | H | Cl | $CF_3$ | H | $CF_3$ | 286–287 | 32.56 | 32.98 | 1.04 | 0.70 | 14.59 | 14.71 |
| 17 | Cl | H | Cl | COOET | H | ME | 236–239 | 41.86 | 41.75 | 3.02 | 2.79 | 16.28 | 16.16 |
| 18* | Cl | H | Cl | COOH | H | ME | 120–139DE | 37.15 | 37.03 | 2.38 | 2.02 | 16.70 | 17.16 |
| 19 | Cl | H | Cl | OH | H | ME | 280–304DE | 38.51 | 38.52 | 2.41 | 2.49 | 18.72 | 19.03 |
| 20 | F | H | F | H | H | H | 296–299DE | 42.46 | 42.27 | 2.25 | 2.30 | 22.52 | 22.60 |
| 21 | Cl | ME | Cl | H | H | H | 253–255DE | 40.23 | 40.00 | 2.51 | 2.65 | 19.55 | 19.75 |
| 22 | F | ME | F | H | H | H | 280–283DE | 44.32 | 44.10 | 2.77 | 2.81 | 21.55 | 21.55 |
| 23 | F | H | F | $CF_3$ | H | ME | 234–237 | 39.74 | 39.49 | 2.04 | 2.08 | 17.83 | 18.11 |
| 24 | Cl | ME | Cl | $CF_3$ | H | ME | 252–254 | 38.21 | 38.09 | 2.27 | 2.34 | 15.97 | 16.40 |
| 25 | F | ME | F | $CF_3$ | H | ME | 243–245 | 41.32 | 41.21 | 2.46 | 2.51 | 17.23 | 17.49 |
| 26 | OME | H | $CF_3$ | H | H | H | 230–232 | 41.80 | 41.40 | 2.68 | 2.77 | 18.78 | 18.69 |
| 27 | Cl | H | Cl | OH | H | OH | 306–308 | 33.51 | 33.27 | 2.3 | 2.5 | 17.77 | 18.04 |
| 28 | Cl | H | Cl | Cl | H | Cl | 154–210DE | 31.98 | 31.54 | 1.72 | 1.77 | 16.96 | 17.41 |
| 29 | Cl | H | Cl | OME | H | OME | 232–234DE | 38.62 | 37.91 | 2.74 | 2.77 | 17.33 | 17.72 |
| 27 | OME | H | $CF_3$ | $CF_3$ | H | ME | 226–229 | 39.61 | 39.50 | 2.42 | 2.52 | 15.40 | 15.60 |
| 28 | OME | H | $CF_3$ | ME | H | ME | 246–249 | 44.91 | 44.77 | 3.49 | 3.61 | 17.47 | 7.94 |
| 29 | Cl | H | Cl | $NME_2$ | H | ME | 280 + DE | 41.90 | 41.70 | 3.49 | 3.48 | 20.95 | 0.82 |
| 30 | Cl | H | Cl | Cl | H | ME | 218–221 | 36.7 | 36.69 | 2.04 | 2.13 | 17.84 | 17.93 |
| 31 | Cl | H | Cl | OME | H | ME | 214–215 | 40.21 | 39.84 | 2.84 | 3.008 | 18.04 | 17.99 |
| 32 | Cl | H | Cl | SME | H | ME | 300–304DE | 38.61 | 38.99 | 2.72 | 2.93 | 17.32 | 17.34 |
| 33 | Cl | H | Cl | $OCH_2CF_3$ | H | ME | 250–245 | 36.85 | 36.8 | 2.19 | 2.21 | 15.35 | 15.63 |
| 34 | Cl | H | Cl | Cl | ME | ME | 260–262 | 36.71 | 37.03 | 2.46 | 2.63 | 17.22 | 16.91 |
| 35 | Cl | H | Cl | Cl | ME | ME | 260–262* | 36.71 | 37.03 | 2.46 | 2.63 | 17.41 | 17.52 |
| 36 | Cl | H | Cl | OH | ME | ME | 310+ | 40.21 | 40.02 | 2.83 | 2.88 | 18.04 | 18.29 |
| 37 | Cl | H | Cl | OME | ME | ME | 210–215DE | 41.79 | 41.41 | 3.23 | 3.29 | 17.41 | 17.52 |
| 38 | Cl | H | Cl | $NME_2$ | ME | ME | 269–272 | | | | | | |
| 39 | Cl | H | Cl | OH | H | OH | 306–208DE | 39.9 | 40.36 | 3.35 | 3.32 | 16.6 | 16.08 |
| 40 | Cl | H | Cl | $NH_2$ | H | ME | >310 | | | | | | |
| 41 | Cl | H | Cl | OME | H | CL | 200–203 | | | | | | |
| 42 | Cl | H | Cl | OME | H | OME | 232–234DE | 38.62 | 37.91 | 2.74 | 2.77 | 17.33 | 17.72 |
| 43 | OME | H | $CF_3$ | SME | H | ME | 245–249 | 41.56 | 41.42 | 3.26 | 3.25 | 16.16 | 16.3 |
| 44 | OME | H | $CF_3$ | OME | H | ME | 205–210 | 43.16 | 42.92 | 3.38 | 3.44 | 16.78 | 16.88 |

*Compound present as monohydrate

Many of the compounds of the present invention are herbicides when applied to the locus of vegetation, herein defined as encompassing preemergent (soil) applications as well as postemergent (foliar) applications. They have utility for broadspectrum pre- and/or post-emergence weed control in areas where complete vegetation control is desired. The subject compounds may also be useful for selective pre- and/or postemergence weed control in crops such as wheat. Certain of these compounds are effective for the control of nutsedge (cyperus spp.) and some compounds may be used for selective weed control in crops such as soybeans, corn or rice.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can be also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat=7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic=61 (molecular weight about 1000), polyethylene glycol ester of tall oil acids, sodium octophenoxyethoxyethyl sulfate, tris(polyoxyethylene)sorbitan monostearate (Tween=60), and sodium dihexylsulfosuccinate.

The herbicidally effective concentration of the active ingredients in solid or liquid compositions generally is from about 0.00003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15 to 50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including the substituted urea herbicides such as 3-(3,4-dichlorophenyl)-1,1-dimethylurea, 3-(3,4-dichlorophenyl)-1-methoxy-1-methylurea (Lorox®) and 1,1-dimethyl-3-(α, α, α-trifluoro-m-tolyl)urea (Cotoran®); the triazines such as 2-chloro-4-(ethylamino)-6-(isopropylamino)-s-triazine and 2-chloro-4-(1-cyano-1-methylethylamino)-6-ethylamino-s-triazine (Bladex®); the uracils such as 5-bromo-3-sec-butyl-6-methyluracil; N-(phosphonomethyl)glycine; the phenoxys such as 2,4-dichlorophenoxyacetic acid; picolinic acids such as 4-amino-3,5,6-trichloropicolinic acid (Tordon®) and 3,6-dichloropicolinic acid (Lontrel®); 4-chloro-2-butynyl-3-chlorophenyl carbamate (Carbyne®); diisopropylthiocarbamic acid, ester with 2,3-dichloroallyl alcohol (Avadex®); diisopropylthiocarbamic acid, ester with 2,3,3-trichloroallyl alcohol (Avadex®BVD); ethyl-N-benzoyl-N-(3,4-dichlorophenyl)-2-aminopropionate (Suffix®); 1,2-dimethyl-3,5-diphenylpyrazolium methylsulfate (Avenge®); methyl (2-[4-(2,4-dichlorophenoxy)phenoxy]propanoate) (Hoelon®); butyl 2-[4-[(5-(trifluoromethyl)-2-pyridinyl)oxy]phenoxy]propanoate (Fusilade®); esters of 2-[4-[(3-chloro-5-trifluoromethyl)-2-pyridinyl)oxy]phenoxy]propionic acid; 4-amino-6-tert-butyl-3-(methylthio)-1,2,4-triazin-5-(4H)-one (Lexone®); 3-isopropyl-1H-2,1,3-benzothiadiazin-(4)-3H-one 2,2-dioxide; α, α, α-trifluoro-2,6-dinitro-N,N-dipropyl-p-toluidine; 1,1'-dimethyl-4,4'-bipyridinium ion; 2-chloro-2',6'-diethyl-(methoxymethyl)acetanilide; and 2-[1-(ethoxyimino)-butyl]-5-[(2-ethylthio)propyl]-3-hydroxy-2-cyclohexen-1-one (Poast®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species. In non-selective preemergence and foliar treatments, the active ingredients of the invention are usually applied at an approximate rate of from about 0.01 to about 20 pounds/acre. In pre- and postemergence operations for selective uses, a dosage of about 0.01 to about 10 pounds/acre is generally applicable, a rate of 0.01 to 4 pounds/acre being preferred.

The following example illustrates the effect of the compounds of this invention applied postemergently.

Plant species in this and other tests were the following:

| | Common Name | Scientific Name |
|---|---|---|
| A. | cotton | Gossypium spp. |
| B. | rape | Brassica napus |
| C. | soybean | Glycine max. |
| D. | sugar beet | Beta saccharifera |
| E. | cocklebur | Xanthium spp. |
| F. | jimsonweed | Datura stramonium |
| G. | annual morning glory | Ipomoea spp. |
| H. | pigweed | Amaranthus spp |
| I. | velvetleaf | Abutilon theophrasti |
| J. | corn | Zea mays |
| K. | rice | Oryza sativa |
| L. | sorghum | Sorghum vulgare |
| M. | wheat | Triticum aestivum |
| N. | barnyardgrass (watergrass) | Echinochloa crusgalli |
| O. | crabgrass | Digitaria spp. |
| P. | yellow foxtail | Setaria lutescens |
| Q. | johnson grass | Sorghum halepense |
| R. | wild oats | Avena fatua |
| S. | yellow nutsedge | Cyperus esculentus |

EXAMPLE 15

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to approximately the 2-4 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postemergent control obtained are set forth in the table below. Control refers to the reduction in growth compared to the observed results of the same untreated species (NT=not tested).

| Compound | Dosage ppm | PLANT SPECIES | | | | | | | | | | | | | | | | | |
|---|---|---|---|---|---|---|---|---|---|---|---|---|---|---|---|---|---|---|---|
| | | A | B | C | D | E | F | G | H | I | J | K | L | M | N | O | P | Q | R | S |
| 1 | 2000 | 40 | 0 | 0 | 100 | 0 | 50 | 50 | 0 | 60 | 50 | 0 | 0 | 0 | 0 | 0 | 40 | 20 | 40 | 0 |
| 2 | 2000 | 85 | 80 | 100 | 100 | 30 | 100 | 100 | 30 | 80 | 50 | 30 | 0 | 20 | 70 | 80 | 80 | 50 | 75 | 80 |
| 3 | 2000 | 85 | 75 | 95 | 100 | 50 | 98 | 95 | 65 | 80 | 40 | 85 | 0 | 0 | 65 | 80 | 80 | 80 | 70 | 80 |
| 4 | 2000 | 85 | 0 | 80 | 100 | 0 | 98 | NT | 0 | 80 | 50 | 25 | 0 | 0 | 0 | 0 | 80 | 40 | 0 | 70 |
| 5 | 2000 | 70 | 0 | 20 | NT | 98 | 70 | 80 | 0 | 50 | 30 | 0 | 0 | 0 | 0 | 0 | 50 | 0 | 0 | 0 |
| 6 | 2000 | 98 | 100 | 80 | 100 | 50 | 100 | 100 | 25 | 98 | 85 | 20 | 0 | 0 | 25 | 0 | 90 | 100 | 70 | 98 |
| 7 | 2000 | 85 | 80 | 85 | 95 | 30 | 90 | 90 | 0 | 80 | 60 | 30 | 0 | 0 | 50 | 50 | 70 | 50 | 65 | 80 |
| 8 | 2000 | 60 | 0 | 0 | 98 | 0 | 100 | 80 | 0 | 80 | 50 | 30 | 0 | NT | 0 | 0 | 80 | 70 | 0 | 0 |
| 9 | 2000 | 30 | 0 | 0 | NT | 0 | 20 | 0 | 0 | 0 | 0 | 0 | 0 | 0 | 0 | 0 | 0 | NT | 0 | 0 |
| 10 | 2000 | 90 | 50 | 0 | 98 | 20 | 90 | 80 | 0 | 30 | 50 | 0 | 0 | 0 | 0 | 0 | 50 | 70 | 0 | 50 |
| 11 | 2000 | 85 | 75 | 0 | 100 | 20 | 95 | NT | 0 | 90 | 90 | 0 | 0 | 0 | 0 | 0 | 90 | NT | 55 | 50 |
| 14 | 500 | NT | NT | 0 | 100 | 80 | 100 | 100 | 100 | 70 | 80 | 40 | 80 | 0 | 70 | 90 | 75 | 80 | 45 | 55 |
| 15 | 250 | 60 | NT | 40 | 100 | 70 | 70 | 80 | 100 | 80 | NT | 35 | 30 | 20 | 80 | 65 | 75 | 80 | 50 | 60 |
| 16 | 4000 | 0 | 0 | 0 | 0 | 0 | 0 | 0 | 0 | 0 | 0 | 0 | 0 | 0 | 0 | 0 | 0 | 0 | 0 | 0 |
| 17 | 2000 | NT | NT | 50 | 100 | 20 | 60 | 30 | 100 | 80 | 20 | 0 | 20 | 0 | 25 | 70 | 80 | 50 | 0 | 65 |
| 18 | 2000 | 0 | NT | 30 | 50 | 0 | 0 | 20 | 98 | 30 | 0 | 0 | 0 | 0 | 0 | 75 | 75 | 0 | 0 | 70 |
| 19 | 2000 | 0 | NT | 0 | 70 | 40 | 0 | 0 | 0 | 70 | 0 | 20 | 0 | 0 | 0 | 15 | 0 | 0 | NT | 0 |
| 20 | 125 | 70 | 100 | 40 | 80 | 80 | 80 | 50 | 100 | 85 | 0 | 80 | 50 | 30 | NT | 60 | 85 | 70 | 0 | 0 |

-continued

| | | PLANT SPECIES | | | | | | | | | | | | | | | | | |
|---|---|---|---|---|---|---|---|---|---|---|---|---|---|---|---|---|---|---|---|
| Compound | Dosage ppm | A | B | C | D | E | F | G | H | I | J | K | L | M | N | O | P | Q | R | S |
| 21 | 125 | 60 | 98 | 50 | 100 | 100 | 85 | 90 | 100 | 100 | 0 | 0 | 65 | 20 | NT | 20 | 100 | 80 | 0 | 40 |
| 22 | 125 | 90 | 100 | 65 | 100 | 100 | 95 | 100 | 100 | 90 | 0 | 100 | 95 | 30 | NT | 80 | 100 | 100 | 50 | 35 |
| 23 | 125 | 0 | 50 | 0 | 80 | 90 | 50 | 0 | 100 | 40 | 20 | 0 | 0 | 0 | NT | 80 | NT | 60 | 0 | 0 |
| 24 | 125 | 30 | 100 | 80 | 100 | 100 | 60 | 70 | 100 | 98 | 0 | NT | 0 | 0 | NT | 20 | 70 | 50 | 0 | 20 |
| 25 | 125 | 0 | 70 | 50 | 80 | 70 | 80 | 35 | 100 | 85 | 80 | NT | 55 | 0 | NT | 0 | 55 | 70 | 0 | 50 |
| 26 | 125 | 60 | 98 | 80 | 100 | 70 | 98 | 90 | 100 | 98 | 0 | 80 | 65 | 50 | NT | 0 | 100 | 80 | 70 | 80 |
| 27 | 125 | 25 | 98 | 65 | 100 | 80 | 100 | 100 | 100 | 85 | 100 | 90 | 100 | 90 | NT | 100 | 100 | 100 | 60 | 75 |
| 28 | 125 | 65 | 95 | 90 | 100 | 85 | 100 | 100 | 100 | 100 | 100 | 100 | 100 | 80 | NT | 100 | 100 | 100 | 80 | 80 |
| 29 | 4000 | 75 | 0 | 0 | 0 | 0 | 0 | 60 | 100 | 85 | 0 | 0 | 0 | 0 | 0 | 75 | 60 | 0 | 50 | 0 |
| 30 | 4000 | 0 | NT | NT | NT | NT | NT | 40 | 100 | 45 | NT | NT | NT | NT | NT | 0 | 0 | NT | 95 | 0 |
| 31 | 4000 | 100 | NT | NT | NT | NT | NT | 90 | 100 | NT | NT | NT | NT | NT | NT | 98 | NT | NT | 100 | 70 |
| 32 | 4000 | 100 | NT | NT | NT | NT | NT | 90 | 100 | 98 | NT | NT | NT | NT | NT | 98 | 100 | NT | 100 | 70 |
| 35 | 1000 | NT | 80 | 25 | NT | NT | NT | NT | 85 | 30 | NT | NT | NT | NT | NT | NT | 100 | NT | NT | NT |
| 36 | 125 | 50 | 90 | 60 | 80 | NT | 50 | NT | 90 | 50 | NT | NT | 35 | NT | NT | NT | 70 | NT | NT | 20 |
| 39 | 2000 | 0 | 70 | 50 | 20 | 0 | 35 | 0 | 80 | 0 | 0 | 20 | 0 | 0 | 0 | 80 | 100 | 0 | 0 | 0 |
| 40 | 250 | 60 | 100 | 98 | 100 | 80 | 100 | 80 | 100 | 100 | 100 | 98 | 80 | 30 | 75 | 95 | 100 | 100 | 90 | 0 |
| 41 | 62.5 | 100 | 98 | 98 | 80 | 100 | 100 | 80 | 100 | 100 | 100 | 98 | 100 | 90 | 100 | 98 | 100 | 100 | 100 | 80 |
| 42 | 62.5 | 98 | 80 | 98 | 85 | 100 | 100 | 70 | 100 | 100 | 100 | 98 | 98 | 100 | 80 | 50 | 100 | 98 | 100 | 70 |
| 43 | 62.5 | 100 | 100 | 98 | 95 | 100 | 100 | 80 | 100 | 100 | 100 | 98 | 100 | 100 | 85 | 98 | 100 | 100 | 100 | 80 |
| 44 | 2000 | 98 | NT | NT | NT | NT | NT | 99 | 99 | 90 | NT | NT | NT | NT | 60 | 98 | 70 | NT | 0 | 0 |

So as to clearly illustrate the phytotoxic properties of the various active ingredients of the present invention applied preemergently, a controlled greenhouse experiment is described below.

EXAMPLE 16

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment the seed beds were maintained for two weeks under greenhouse conditions conducive for good plant growth and watered as necessary. The specific plant species, test compound, and dosage and the percent preemergent control are set forth in the table below. Control refers to the reduction in growth compared to the observed results of the same untreated species.

| | | PLANT SPECIES | | | | | | | | | | | | | | | | | |
|---|---|---|---|---|---|---|---|---|---|---|---|---|---|---|---|---|---|---|---|
| Compound | Dosage lbs/a | A | B | C | D | E | F | G | H | I | J | K | L | M | N | O | P | Q | R | S |
| 16 | 10 | 0 | 0 | 0 | 0 | 0 | 0 | 0 | 80 | 60 | 0 | 0 | 0 | 0 | 0 | 0 | 0 | 0 | 0 | 0 |
| 33 | 10 | 40 | 0 | 0 | 0 | 0 | 0 | 0 | 100 | 40 | 0 | 0 | 0 | 0 | 0 | 100 | 100 | 0 | 0 | 0 |
| 38 | 10 | 0 | 0 | 0 | 0 | 0 | 0 | 0 | 0 | 0 | 0 | 0 | 0 | 0 | 0 | 100 | 0 | 0 | 100 | 0 |

What is claimed is:

1. A compound having the formula

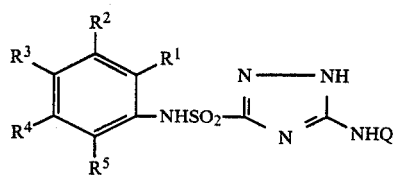

wherein Q is H or COX, X represents H, $C_1-C_4$ alkyl or phenyl, $R^1$ through $R^5$ individually represent H or from 1 to 3 substituents chosen from $C_1-C_4$ alkyl or halo substituted alkyl, halo, $-NO_2$, $-Ar$, $-OAr$, $-CF_3$, $-OCF_3$, $-OCF_2CF_2H$, $-OCF_2CCl_2H$, $-OCH_2CF_3$, $-SO_2CF_3$, $-SO_2CF_2F_2H$, $-SO_2CF_2CCl_2H$, $-SO_2R^6$, $-COOR^6$, $-CONH_2$, $-CONHR^7$, $-CONR^7(R^8)$, $-SO_3R^7$, and $-SO_3CH_2CF_3$, $-SR^6$, $-OR^7$, $-CR^6R^6R6$, and $-NR6R6$, wherein Ar represents substituted or unsubstituted phenyl or pyridyl wherein the substituents are haol, $C_1-C_4$ alkyl or $C_1-C_4$ haloalkyl, $R^6$ represents H, phenyl or $C_1-C_4$ alkyl, and $R^7$ and $R^8$ individually represent $C_1-C_4$ alkyl.

2. Compound of claim 1 wherein Q is H.
3. Compound of claim 1 wherein Q is COX.
4. Compound of claim 3 wherein Z is $CH_3$.
5. Compound of claim 3 wherein X is H.
6. Compound of claim 2 wherein $R^1$ and $R^5$ are chloro and $R^2$, $R^3$ and $R^4$ are hydrogen.
7. Compound of claim 4 wherein $R^1$ and $R^5$ are chloro and $R^2$, $R^3$ and $R^4$ are hydrogen.
8. Compound of claim 5 wherein $R^1$ and $R^5$ are fluoro, $R^2$ is methyl and $R^3$ and $R^4$ are hydrogen.
9. Compound of claim 5 wherein $R^1$ is chloro, $R^5$ is methylphenyl and $R^2$, $R^3$ and $R^4$ are hydrogen.
10. A composition comprising an inert carrier in admixture with a herbicidally effective amount of a compound or a salt of a compound of claim 1.
11. Method of controlling undesired vegetation which comprises the application to the locus of said vegetation of a herbicidally effective amount of a compound of claim 1.

* * * * *

UNITED STATES PATENT AND TRADEMARK OFFICE
CERTIFICATE OF CORRECTION

PATENT NO. : 4,734,123
DATED : March 29, 1988
INVENTOR(S) : William T. Monte

It is certified that error appears in the above-identified patent and that said Letters Patent is hereby corrected as shown below:

Col. 6, line 47, delete "(2.6" and insert -- (2,6 --;

Col. 7, line 68, delete "22.8" and insert -- 22.18 --;

Col. 9, line 39, delete "8.04" and insert -- 18.04 --;

Col. 9, line 68, after "1" insert -- ml --;

Col. 18, line 24, delete "$C_1-C_4$" and insert -- $C_1-C_6$ --;

Col. 18, line 30, delete "-CONH$_2$, CONHR$^7$" and insert -- -CONH$_2$, -CONHR$^7$ --;

Col. 18, line 32, delete "-CR$^6$R$^6$R6, and -NR6R6" and insert -- -CR$^6$R$^6$OR$^6$, and -NR$^6$R$^6$ --;

Col. 18, line 34, "halo" has been misspelled;

Col. 18, line 39, delete "Z" and insert -- X --.

Signed and Sealed this

Seventh Day of February, 1989

Attest:

DONALD J. QUIGG

Attesting Officer     Commissioner of Patents and Trademarks